(12) United States Patent
Abels et al.

(10) Patent No.: US 7,234,935 B2
(45) Date of Patent: *Jun. 26, 2007

(54) ORTHODONTIC BRACKET SYSTEM COMPRISING MULTIPLE BRACKETS HAVING MULTIPLE ALIGNED SLOTS

(76) Inventors: Norbert Abels, Alleestraβe 30a, 66424, Homburg (DE); Claus-H. Backes, St. Wendeler Straβe 45, 66113, Saarbrücken (DE)

( * ) Notice: Subject to any disclaimer, the term of this patent is extended or adjusted under 35 U.S.C. 154(b) by 78 days.

This patent is subject to a terminal disclaimer.

(21) Appl. No.: 10/836,014

(22) Filed: Apr. 29, 2004

(65) Prior Publication Data

US 2005/0244774 A1 Nov. 3, 2005

(51) Int. Cl.
 *A61C 3/00* (2006.01)
(52) U.S. Cl. ............... 433/8; 433/10; 433/11
(58) Field of Classification Search ............ 433/10–13, 433/8, 17, 14
See application file for complete search history.

(56) References Cited

U.S. PATENT DOCUMENTS

| | | | | |
|---|---|---|---|---|
| 3,469,315 A | 9/1969 | Russ | ............... | 32/14 |
| 3,477,128 A | 11/1969 | Andrews | ............... | 32/14 |
| 3,660,900 A * | 5/1972 | Andrews | ............... | 433/16 |
| 3,748,740 A | 7/1973 | Wildman | ............... | 32/14 |
| 4,014,096 A | 3/1977 | Dellinger | ............... | 32/14 A |
| 4,077,126 A | 3/1978 | Pletcher | ............... | 32/14 |
| 4,492,573 A * | 1/1985 | Hanson | ............... | 433/11 |
| 4,597,739 A | 7/1986 | Rosenberg | ............... | 433/16 |
| 4,669,981 A | 6/1987 | Kurz | ............... | 433/9 |
| 4,676,746 A | 6/1987 | Klapper | ............... | 433/16 |
| 4,698,017 A * | 10/1987 | Hanson | ............... | 433/11 |
| 4,712,999 A * | 12/1987 | Rosenberg | ............... | 433/8 |
| RE34,044 E | 8/1992 | Broussard | ............... | 433/8 |
| 5,169,311 A | 12/1992 | Lee | ............... | 433/14 |
| 5,226,814 A | 7/1993 | Allen | ............... | 433/15 |
| 5,248,257 A | 9/1993 | Cannon | ............... | 433/14 |
| 5,344,315 A * | 9/1994 | Hanson | ............... | 433/20 |
| 5,374,187 A | 12/1994 | Vashi | ............... | 433/8 |
| 5,395,238 A | 3/1995 | Andreiko et al. | ............... | 433/24 |
| 5,556,277 A | 9/1996 | Yawata et al. | ............... | 433/17 |
| 5,562,444 A * | 10/1996 | Heiser et al. | ............... | 433/11 |
| 5,630,716 A * | 5/1997 | Hanson | ............... | 433/14 |
| 5,700,145 A * | 12/1997 | Wildman | ............... | 433/10 |
| 5,791,897 A | 8/1998 | Wildman | ............... | 433/10 |
| 5,823,771 A | 10/1998 | Nord | ............... | 433/14 |
| 5,857,849 A * | 1/1999 | Kurz | ............... | 433/10 |
| 5,906,486 A * | 5/1999 | Hanson | ............... | 433/11 |
| 5,993,206 A | 11/1999 | Andreiko | ............... | 433/9 |
| 6,071,118 A | 6/2000 | Damon | ............... | 433/9 |
| 6,071,119 A * | 6/2000 | Christoff et al. | ............... | 433/14 |
| 6,264,468 B1 | 7/2001 | Takemoto | ............... | 433/8 |
| 6,506,049 B2 * | 1/2003 | Hanson | ............... | 433/11 |
| 2003/0096209 A1 | 5/2003 | Sugiyama et al. | ............... | 433/8 |

* cited by examiner

*Primary Examiner*—Cary E. O'Connor
(74) *Attorney, Agent, or Firm*—Workman Nydegger (57) ABSTRACT

An orthodontic bracket system includes a plurality of orthodontic brackets, each bracket sized and configured to be placed on a particular tooth of a patient during an orthodontic treatment procedure. Each bracket includes at least two arch wire slots that lie in different planes. The arch wire slots are positioned relative to the bracket base so that when the patient's teeth have become properly aligned as a result of the orthodontic procedure, the corresponding arch wire slots of all the brackets will be substantially aligned.

24 Claims, 6 Drawing Sheets

ORTHODONTIC BRACKET SYSTEM COMPRISING MULTIPLE BRACKETS HAVING MULTIPLE ALIGNED SLOTS

BACKGROUND OF THE INVENTION

1. The Field of the Invention

The present invention relates to orthodontic brackets, more particularly to orthodontic bracket systems for use during orthodontic procedures.

2. The Relevant Technology

Orthodontics is a specialized field of dentistry that involves the application of mechanical forces to urge poorly positioned, or crooked, teeth into correct alignment and orientation. Orthodontic procedures can be used for cosmetic enhancement of teeth, as well as medically necessary movement of teeth to correct underbites or overbites. For example, orthodontic treatment can improve the patient's occlusion, or enhance spatial matching of corresponding teeth.

The most common form of orthodontic treatment involves the use of orthodontic brackets and wires, which together are commonly referred to as "braces". Orthodontic brackets, more particularly the orthodontic bases, are small slotted bodies configured for direct attachment to the patient's teeth or, alternatively, for attachment to bands which are, in turn, cemented or otherwise secured around the teeth. Once the brackets are affixed to the patient's teeth, such as by means of glue or cement, a curved arch wire is inserted into the slot of each bracket. The arch wire acts as a template or track to guide movement of the teeth into proper alignment. End sections of the arch wire are typically captured within tiny appliances known as "buccal tubes" affixed to the patient's molars.

Customarily, an arch wire is held within the arch wire slot by ligatures. More recently, self-ligating brackets have been developed that eliminate the need for separate ligatures. Self-ligating brackets may include a cover associated with the bracket base that closes over and secures the arch wire within the arch wire slot. Examples of self-ligating brackets are disclosed in U.S. Pat. Nos. 3,748,740, 4,077,126, 5,857, 849, and 6,071,118.

In using an arch wire to apply corrective forces to each tooth, elaborate bends of the arch wire are often necessary to create the desired force to make the intended correction. Elaborate bends of the arch wire are necessary to account for the fact that arch wire slots of the various brackets of existing bracket systems are oriented in different planes. As the teeth are moved to their corrected positions, the planes of the various arch wire slots do not become aligned, necessitating the elaborate bends. These bends can be difficult and time consuming to form, and mistakes in the choice and formation of bends can move the teeth in unwanted directions.

It would be an improvement in the art to provide an orthodontic bracket system where such elaborate bends of the arch wire were not required or were minimized.

In addition, it would be an improvement in the art to provide an orthodontic bracket system with brackets having multiple arch wire slots so as to allow use of multiple arch

BRIEF SUMMARY OF THE INVENTION

The orthodontic bracket system of the present invention includes a plurality of orthodontic brackets, each bracket sized and configured to be placed on a particular tooth of a patient during an orthodontic treatment procedure. Each bracket includes at least two arch wire slots that lie in different planes. The arch wire slots are positioned relative to the bracket base so that when the patient's teeth have become properly aligned as a result of the orthodontic treatment procedure, the corresponding arch wire slots of all the brackets will be substantially aligned. This, in turn, allows for the continual use of arch wires that remain "straight" throughout the procedure (i.e., that have a "straight" or regular curvature with little or no abrupt or irregular bends).

The orthodontic brackets may be configured for placement on either the upper or lower dental arch. For example, the system may include as few as two or as many as fourteen orthodontic brackets, each bracket being configured for placement on one tooth of the upper or lower dental arch.

Each orthodontic bracket included in the system may be specifically configured for placement on a particular tooth or subset of teeth. Whereas aligning the main arch wire slot may be routine, aligning both the main slot and the secondary or auxiliary slots that lie in a different plane may be challenging because of varying tooth size and orientation in normally aligned teeth and corresponding variations in size and shape of brackets for each tooth.

Because of these variations in the size and angle of various teeth of the dental arch, the various brackets intended for placement on those teeth include arch wire slots oriented differently relative to the bonding surface of the bracket base. The arch wire slots of each orthodontic bracket are formed in the bracket base so that when the brackets are placed on the teeth of the dental arch the arch wire slots are substantially aligned once treatment is complete. When treatment is complete, the arch wire will be evenly and smoothly curved, without the need for any deviating bends (which are elaborate and difficult to form).

The orthodontic brackets of the bracket system are self-ligating, i.e., the arch wire is clamped or otherwise held between the ligation cover and the bracket base. The ligating cover is connected to the bracket base, and the cover is movable relative to the bracket base between an open, non-ligating position relative to the arch wire slots and a closed, ligating position relative to the arch wire slots. In other words, at least two arch wire slots are ligated using a single cover.

These and other advantages and features of the present invention will become more fully apparent from the following description and appended claims, or may be learned by the practice of the invention as set forth hereinafter.

BRIEF DESCRIPTION OF THE DRAWINGS

To further clarify the above and other advantages and features of the present invention, a more particular description of the invention will be rendered by references to specific embodiments thereof, which are illustrated in the appended drawings. It is appreciated that these drawings depict only typical embodiments of the invention and are therefore not to be considered limiting of its scope. The invention will be described and explained with additional specificity and detail through the use of the accompanying drawings in which.

DETAILED DESCRIPTION OF THE PREFERRED EMBODIMENTS

I. Introduction

The orthodontic bracket system of the present invention includes a plurality of orthodontic brackets, each bracket sized and configured to be placed on a particular tooth of a patient during an orthodontic treatment procedure. Each bracket includes at least two arch wire slots that lie in different planes. The arch wire slots are positioned relative to the bracket base so that when the patient's teeth have become properly aligned as a result of the orthodontic procedure, the corresponding arch wire slots of all the brackets will be substantially aligned. In other words, the corresponding arch wire slots of all the brackets are aligned so that an arch wire engaged in the slots is "straight," having little or no abrupt or irregular bends along the length of the arch wire.

The orthodontic brackets of the system may be configured for placement on either the upper or lower dental arch. For example, the system may include as few as two or as many as fourteen orthodontic brackets, each configured for placement on one tooth of the upper or lower dental arch. Separate systems of brackets may be provided for the upper and lower dental arches.

Each orthodontic bracket included in the system may be specifically configured for placement on a particular tooth or subset of teeth. Because of variations in the size and angle of various teeth of an ideal, corrected dental arch, the various brackets intended for placement on those teeth include arch wire slots oriented differently relative to the bonding surface of the bracket base. The arch wire slots of each orthodontic bracket are formed in the bracket base so that when the brackets are placed on the teeth of the dental arch the arch wire slots are substantially aligned once treatment is complete. When treatment is complete, the arch wire will be evenly and smoothly curved, without any deviating bends.

Because of the variation in size, position, and angle of each tooth of an ideal, corrected dental arch, the labial surface of each tooth defines a plane. Each defined plane is unique. In order to use a "straight" arch wire (i.e., one having a regular curvature with little or no abrupt or irregular bends), the arch wire must pass through a point of each plane defined by each corrected tooth. The arch wire slots of each orthodontic bracket bonded to each tooth must be positioned so that the arch wire is "straight." The position and orientation of each arch wire slot is configured to create such an alignment when the teeth have been moved to a correct or ideal configuration.

According to one embodiment, each orthodontic bracket included in the bracket system includes a bracket base, at least two arch wire slots, and a ligating cover. Including at least two arch wire slots allows concurrent treatment of multiple conditions. Alternatively, a dental practitioner may use two (or more) arch wires to treat a single condition, effectively reducing the necessary treatment time. The bracket may optionally be formed as one single piece, requiring no assembly. This reduces the cost and complexity of manufacture and prevents unwanted separation of the bracket parts. Attention is now turned to the drawings, which illustrate an exemplary orthodontic bracket system according to the invention.

II. An Exemplary Orthodontic Bracket System

Orthodontic brackets of various designs may be incorporated in an orthodontic bracket system according to the present invention. FIGS. 1A-3B illustrate various examples of such brackets according to one design. An alternative bracket design is illustrated in FIGS. 4A-5C. These and other bracket designs that could be used are disclosed in U.S. patent application Ser. No. 10/464,615 titled "ORTHODONTIC BRACKET WITH ELONGATE FILM HINGE", now issued U.S. Pat. No. 6,960,081. U.S. patent application Ser. No. 10/782,487 titled "A TWO PART ORTHODONTIC BRACKET," now issued U.S. Pat. No. 6,964,565, and U.S. patent application Ser. No. 10/836,074 titled "MOLAR ORTHODONTIC BRACKETS HAVING A HINGED BRACKET COVER", now published U.S. Application No. 2005/0244775, each of which is herein incorporated by reference.

Figure 1A:
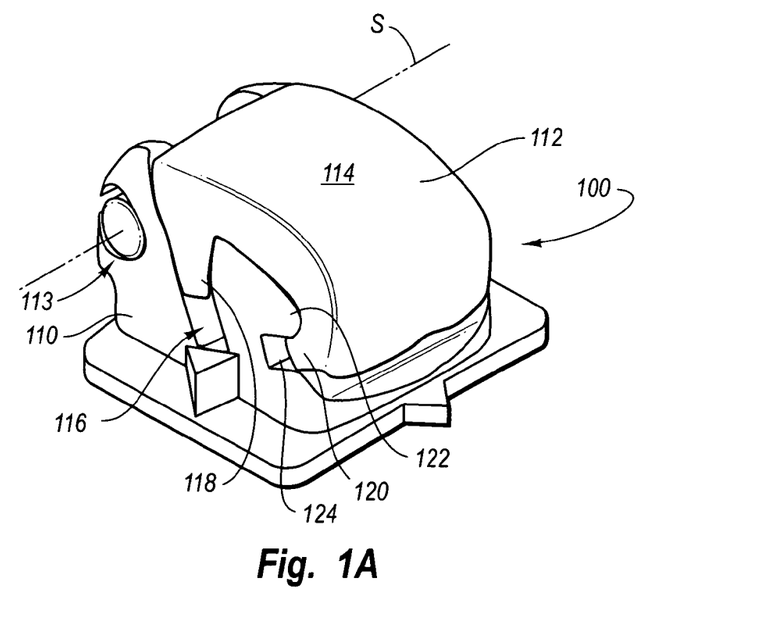
FIGS. 1A-1B are perspective views of one exemplary orthodontic bracket that may be included in a bracket set according to the present invention.

FIG. 1A shows a two-part orthodontic bracket 100 which consists of a base 110 and a ligation cover 112. The base 110 and cover 112 are pivotally connected to each other via a joint 113 which has a horizontal pivot axis S about which the cover 112 can be rotated between open and closed positions.

In the embodiment shown, the cover 112 includes a smooth, curved outer surface 114. It will be appreciated that the cover 112 can have other shapes as desired to yield an orthodontic bracket having a desired configuration and functionality.

As further illustrated in FIG. 1A, the cover 112, while in a completely closed or latched state relative to the base 110, covers or occludes primary arch wire slot 116 designed to receive therein an arch wire (not shown). The cover 112 is advantageously provided with an extension 118 designed to bear against and hold an arch wire in primary slot 116 when the cover 112 is closed or latched relative to the base 110, as better seen in FIG. 1B.

Figure 1B:
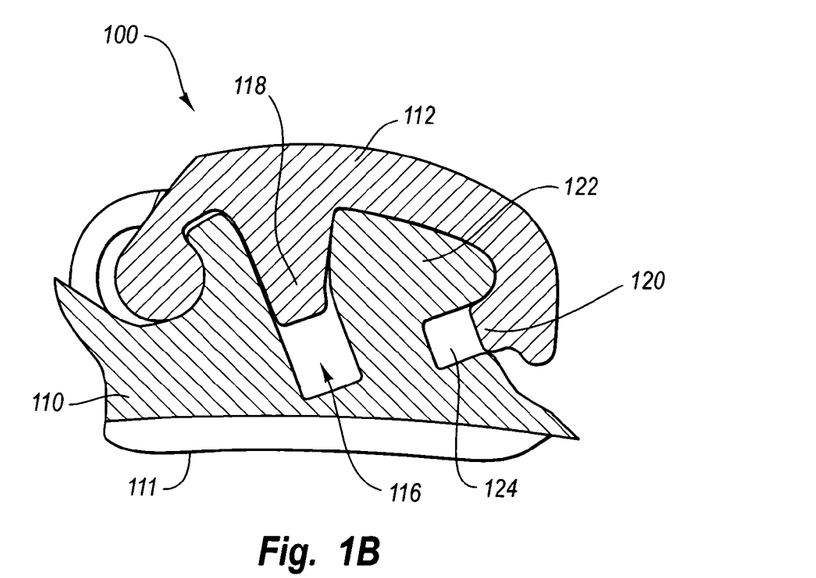

It will be observed that the bottom surfaces of primary and secondary arch wire slots 116 and 124, respectively, are inclined relative to the bonding surface 111 of the base 110. The arch wire slots 116 and 124 are located and oriented within the bracket base 110 so as to be substantially aligned with the other slots of the bracket system once the orthodontic treatment is complete. In other words, the orientation of each slot of each bracket within the bracket system is configured so as to result in all corresponding (e.g., all primary or all secondary) arch wire slots being substantially aligned once the orthodontic treatment is complete. An orthodontic bracket having an arch wire orientation as illustrated in FIGS. 1A-1B may be particularly suited for attachment to the bicuspids. Additional exemplary brackets having different arch wire orientations are will be described in conjunction with FIGS. 2A-3B.

In the closed or latched state, the cover 112 and base 110 of the bracket 100 form a substantially uniformly curved surface 114 having no sharp or jagged corners or edges that might irritate a user of the bracket 100. This prevents or reduces potential injury and discomfort to the patient, as well as the tendency of food or other foreign substances to catch or adhere to the bracket 100.

The bracket 100 may further include a locking mechanism. Cover 112 includes a latch projection 120 provided at an end of the cover 112 distal to the joint 113. The latch projection 120 generally extends toward the base 110 and is configured so as to snap over a latch bump 122 provided at the base 110 in order to mechanically latch the cover 112 to the base 110.

As shown in FIGS. 1A-1B, an secondary arch wire slot 124 may be provided in the base 110 in the region of the latch projection 120, which, in one embodiment, extends parallel to the primary arch wire slot 116 and is likewise covered when the cover 112 is completely closed or latched so as to fix or ligate an arch wire that may optionally be provided in the secondary arch wire slot 124.

The joint 113 is configured so as to permit the cover 112 to have multiple degrees of freedom of movement relative to the base 110 while in the open position. These and other features of the bracket are further disclosed in U.S. patent application Ser. No. 10/782,487 titled "A TWO PART ORTHODONTIC BRACKET," already incorporated herein by reference.

Figure 2A:
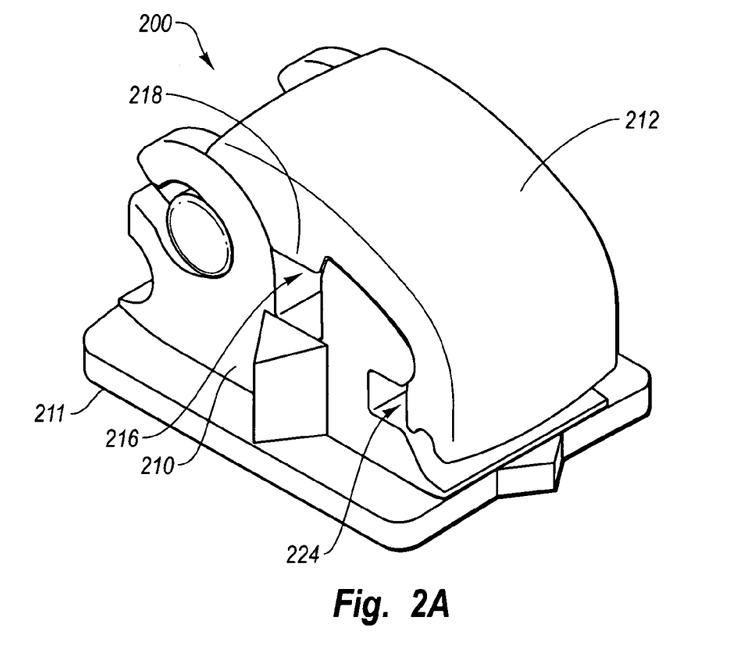
FIGS. 2A-2B are perspective views of one exemplary orthodontic bracket that may be included in a bracket set according to the present invention.
Figure 2B:
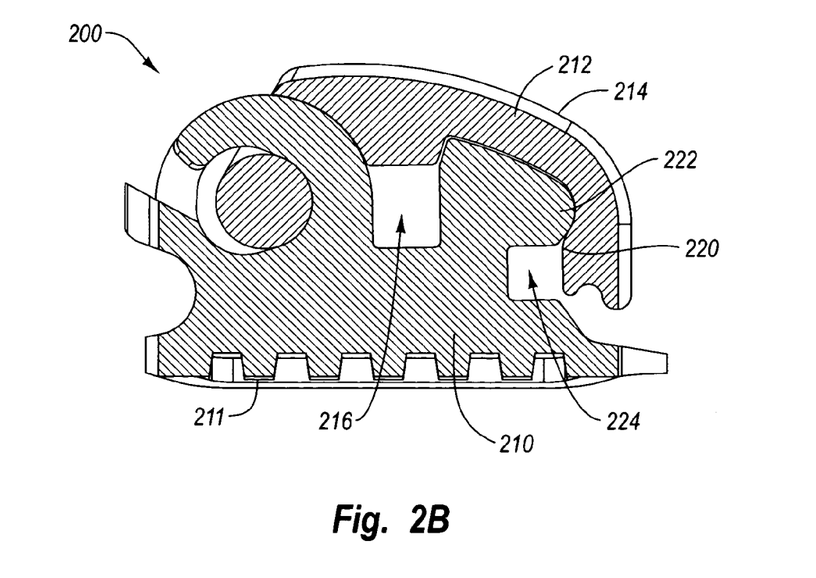

FIGS. 2A-2B illustrate another orthodontic bracket 200 that may be included in a bracket system according to the invention. The bracket 200 includes a bracket base 210, a cover 212 forming a substantially uniformly curved surface 214, a primary arch wire slot 216, a bearing extension 218, a latch projection 220, a latch bump 222, and a secondary arch wire slot 224.

The bottom surface of the primary and secondary arch wire slots 216 and 224, respectively, are parallel relative to the bonding surface 211 of the base 210. The arch wire slots 216 and 224 are located and oriented within the bracket base 210 so as to be substantially aligned with the other slots of the bracket system once the orthodontic treatment is complete. In other words, the orientation of each slot of each bracket within the bracket system is configured so as to result in all corresponding (e.g., all primary or all secondary) arch wire slots being substantially aligned once the orthodontic treatment is complete. An orthodontic bracket having an arch wire orientation as illustrated in FIGS. 2A-2B may be particularly suited for attachment to the incisors.

Figure 3A:
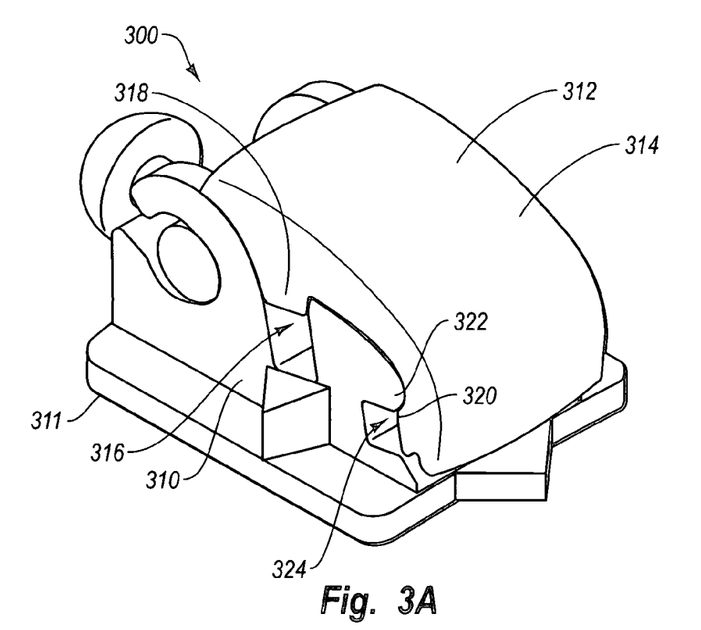
FIGS. 3A-3B are perspective views of one exemplary orthodontic bracket that may be included in a bracket set according to the present invention.
Figure 3B:
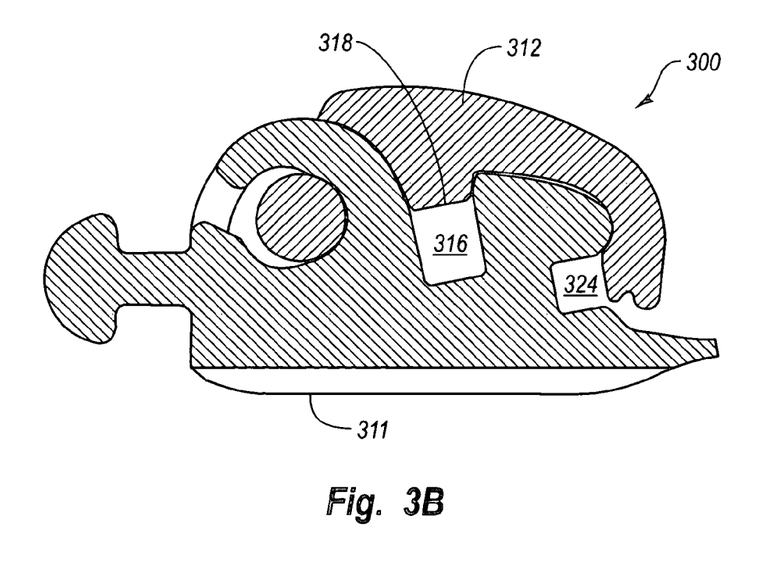

FIGS. 3A-3B illustrate another orthodontic bracket 300 that may be included in a bracket system according to the invention. The bracket 300 includes a bracket base 310, a cover 312 forming a substantially uniformly curved surface 314, a primary arch wire slot 316, a bearing extension 318, a latch projection 320, a latch bump 322, and a secondary arch wire slot 324.

The bottom surface of the primary and secondary arch wire slots 316 and 324, respectively, are inclined relative to the bonding surface 311 of the base 310. The inclination of the bottom of the primary arch wire slot 316 and secondary arch wire slot 324 is less than the inclination of bracket 100 illustrated in FIGS. 1A-1B. The arch wire slots 316 and 324 are located and oriented within the bracket base 310 so as to be substantially aligned with the other slots of the bracket system once the orthodontic treatment is complete. In other words, the orientation of each slot of each bracket within the bracket system is configured so as to result in all corresponding (e.g., all primary or all secondary) arch wire slots being substantially aligned once the orthodontic treatment is complete. An orthodontic bracket having an arch wire orientation as illustrated in FIGS. 3A-3B may be particularly suited for attachment to the canines.

Figure 4A:
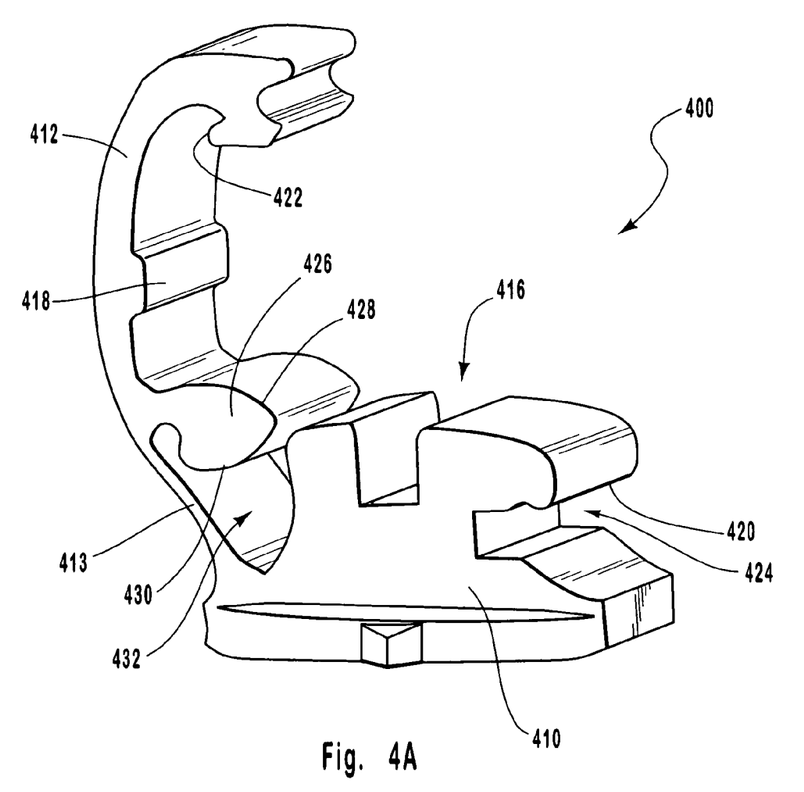
FIG. 4A is a perspective view of an alternative orthodontic bracket design that may be included in the inventive bracket set, and where the bracket is in an open, non-ligating position.
Figure 4B:
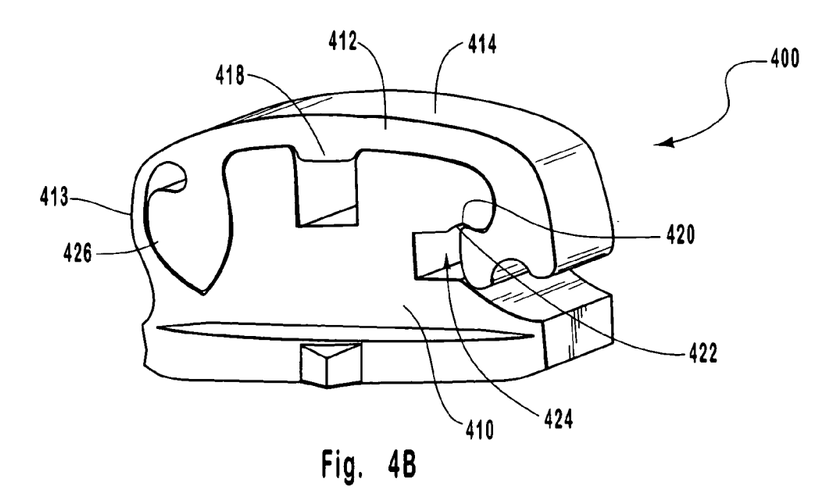
FIG. 4B is a perspective view of an alternative orthodontic bracket design that may be included in the inventive bracket set, and where the bracket is in a closed, ligating position.

FIGS. 4A and 4B depict an alternative orthodontic bracket design. Orthodontic bracket 400 includes a bracket base 410 to which a ligation cover 412 is hinged attached. A primary arch wire slot 416 open to the upper side of the bracket base 410 is provided near the center of the base 410 and serves for the receipt of an arch wire therein. The orthodontic bracket 400 also includes a secondary arch wire slot 424. Ligation of both arch wire slots is accomplished by closing the ligation cover 412 over the bracket base 410. An extension 418 is provided in the cover 412 so as to bear against and hold an arch wire in primary slot 416 when the cover 412 is closed or latched relative to the base 410, as better seen in FIG. 4B.

The orthodontic bracket 400 includes an elongate film hinge 413 that is attached at one end to the bracket base 410 and at an opposite end to the ligation cover 412. In this way, the ligation cover 412 is hinged attached to the bracket base 410 and is able to be as selectively rotated between an open, non-ligating position and a closed, ligating position relative to the bracket base 410, more particularly the arch wire slots 416, 424.

Because the film hinge 413 is elongated, it is able to bend gradually over its entire length rather than at a single point or line. This results in a hinge that is more resilient and durable over time because it is not overly bent or stressed at any particular point or line along its length. Moreover, because the elongate film hinge can bend gradually over substantially its entire length, it can be of a thicker, stronger construction compared to a film hinge that bends at a single point or line. This results in a hinge that is significantly stronger and more resistant to breakage compared to other film hinges. In order to maximize strength while providing sufficient bendability, the elongate film hinge is advantageously formed as thick as possible to provide maximum strength while being sufficiently thin to allow the hinge to bend with sufficient flexibility and resilience when in use.

The illustrated embodiment also includes a curved surface that interacts with the elongate film hinge to assist in causing the hinge to bend gradually along substantially its entire length as the ligation cover is selectively rotated relative to the bracket base. This curved surface may either comprise an integral part of the ligation cover or bracket base, or alternatively, a separate piece attached to the cover or bracket base. In one embodiment, the curved surface may be part of a cam structure that is integrally attached to the ligation cover, as illustrated in FIG. 4A.

In FIG. 4A, a cam structure 426 is illustrated that has a camming surface 428 and a curved hinge-guiding surface 430. The hinge-guiding surface 430 is an example of a curved surface that interacts with the elongate film hinge 413 to assist in gradually bending the film hinge along substantially its entire length as the ligation cover 412 is rotated relative to the bracket base 410. The hinge-guiding surface 430 is advantageously curved so as to interact with the elongate film hinge 413 by distributing forces along substantially its entire length as the ligation cover 412 is rotated. Distributing forces along the length of the elongate film hinge 413, rather than allowing the forces to concentrate at a single location, results in a hinged bracket that is more resistant to breakage of the film hinge compared to brackets in which the film hinge is bent abruptly at a specific point or line. In one embodiment, the hinge-guiding surface 430 may help maintain the ligation cover 412 (in combination a latch mechanism) in the locked position by exerting outward pressure against the elongate film hinge 413. This, in turn, effectively shortens length of the ligation cover 412, thereby causing the exemplary latch mechanism to hold the ligation cover 412 more tightly.

The camming surface 428 is curved or angled in such a way so that it interacts with the bracket base 410 in order to bias the ligation cover 412 toward the open, non-ligating position when the cover is in an unlocked configuration relative to the bracket base 410. This improves access to the arch wire slot 416, making insertion or removal of an arch wire easier.

In the embodiment illustrated in FIG. 4A, cam structure 426 is integrally attached to the inner surface of the ligation cover 412 in a manner so as to extend toward the bracket base 410. Further, and as is shown in particular in FIG. 4B, the cam structure 426 is received within a recess 432 between the bracket base 410 and the elongate film hinge 413 when the ligation cover 412 is in the closed position. This results in a smooth, curved outer surface 414 along both the top of the bracket and along the side.

The orthodontic bracket 400 may advantageously include a latch mechanism. The illustrated embodiment shows a latch mechanism in which increased pressure by an arch wire bearing upwardly against the ligation cover 412 results in tighter locking of the cover 412 to the bracket base 410. In the illustrated embodiment, an angled keyway 420 is provided near one end of the bracket base 410. The ligation cover 412 contains a corresponding locking tongue 422 that is insertable within the angled keyway 420.

Figure 5A:
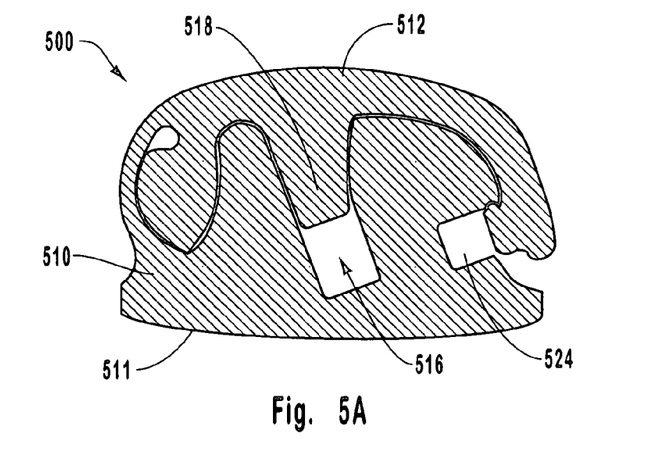
FIGS. 5A-5C are perspective views of various orthodontic brackets after the design of the bracket of FIG. 4A that may be included in a bracket system according to the present invention.

FIG. 5A illustrates a cross sectional view of an exemplary orthodontic bracket 500 according to the basic design of FIG. 4A. The bottom surfaces of primary and secondary arch wire slots 516 and 524, respectively, are inclined relative to the bonding surface 511 of the base 510. The arch wire slots 516 and 524 are located and oriented within the bracket base 510 so as to be substantially aligned with the other slots of the bracket system once the orthodontic treatment is complete. In other words, the orientation of each slot of each bracket within the bracket system is configured so as to result in all corresponding (e.g., all primary or all secondary) arch wire slots being substantially aligned once the orthodontic treatment is complete. An orthodontic bracket having an arch wire orientation as illustrated in FIG. 5A may be particularly suited for attachment to the bicuspids.

Figure 5B:
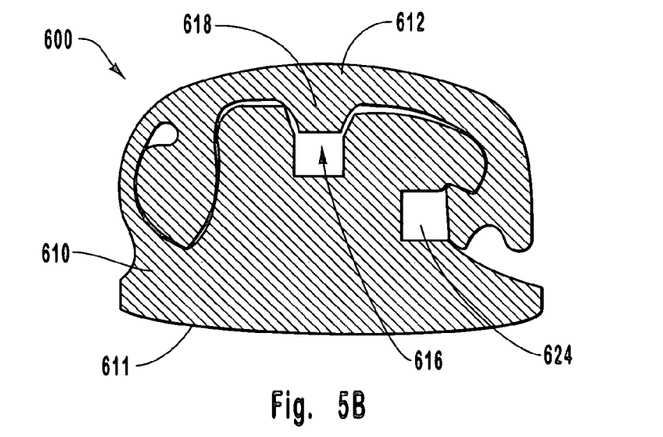

FIG. 5B illustrates a cross sectional view of another exemplary orthodontic bracket 600 according to the basic design of FIG. 4A. The bottom surface of the primary and secondary arch wire slots 616 and 624, respectively, are parallel relative to the bonding surface 611 of the base 610. The arch wire slots 616 and 624 are located and oriented within the bracket base 610 so as to be substantially aligned with the other slots of the bracket system once the orthodontic treatment is complete. In other words, the orientation of each slot of each bracket within the bracket system is configured so as to result in all corresponding (e.g., all primary or all secondary) arch wire slots being substantially aligned once the orthodontic treatment is complete. An orthodontic bracket having an arch wire orientation as illustrated in FIG. 5B may be particularly suited for attachment to the incisors.

Figure 5C:
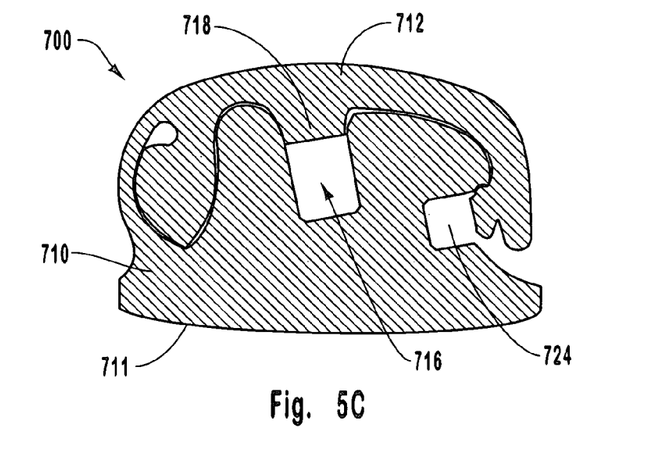

FIG. 5C illustrates a cross sectional view of yet another exemplary orthodontic bracket 700 according to the basic design of FIG. 4A. The bottom surface of the primary and secondary arch wire slots 716 and 724, respectively, are inclined relative to the bonding surface 711 of the base 710. The inclination of the bottom of the primary arch wire slot 716 and secondary arch wire slot 724 is less than the inclination of bracket 500 illustrated in FIG. 5A. The arch wire slots 716 and 724 are located and oriented within the bracket base 710 so as to be substantially aligned with the other slots of the bracket system once the orthodontic treatment is complete. In other words, the orientation of each slot of each bracket within the bracket system is configured so as to result in all corresponding (e.g., all primary or all secondary) arch wire slots being substantially aligned once the orthodontic treatment is complete. An orthodontic bracket having an arch wire orientation as illustrated in FIG. 5C may be particularly suited for attachment to the canines.

Figure 6:
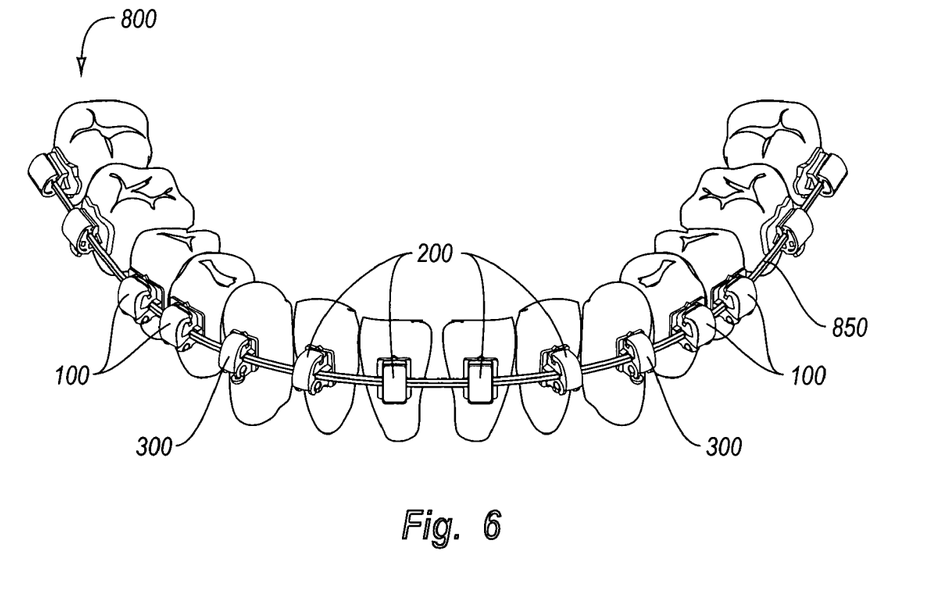
FIG. 6 is a top perspective view of an exemplary bracket system installed wherein the arch wire slots of the various brackets are substantially aligned after treatment is complete.

FIG. 6 illustrates a top perspective view of an upper dental arch 800 with an arch wire 850 once the orthodontic treatment is completed. The arch wire 850 is engaged in a plurality of orthodontic brackets 100, 200, and 300. Orthodontic brackets 100 are positioned on the bicuspids, brackets 200 are positioned on the incisors, and brackets 300 are positioned on the canines. The arch wire 850 is evenly and smoothly curved along the dental arch 800, without any abrupt or irregular bends.

Figure 7:
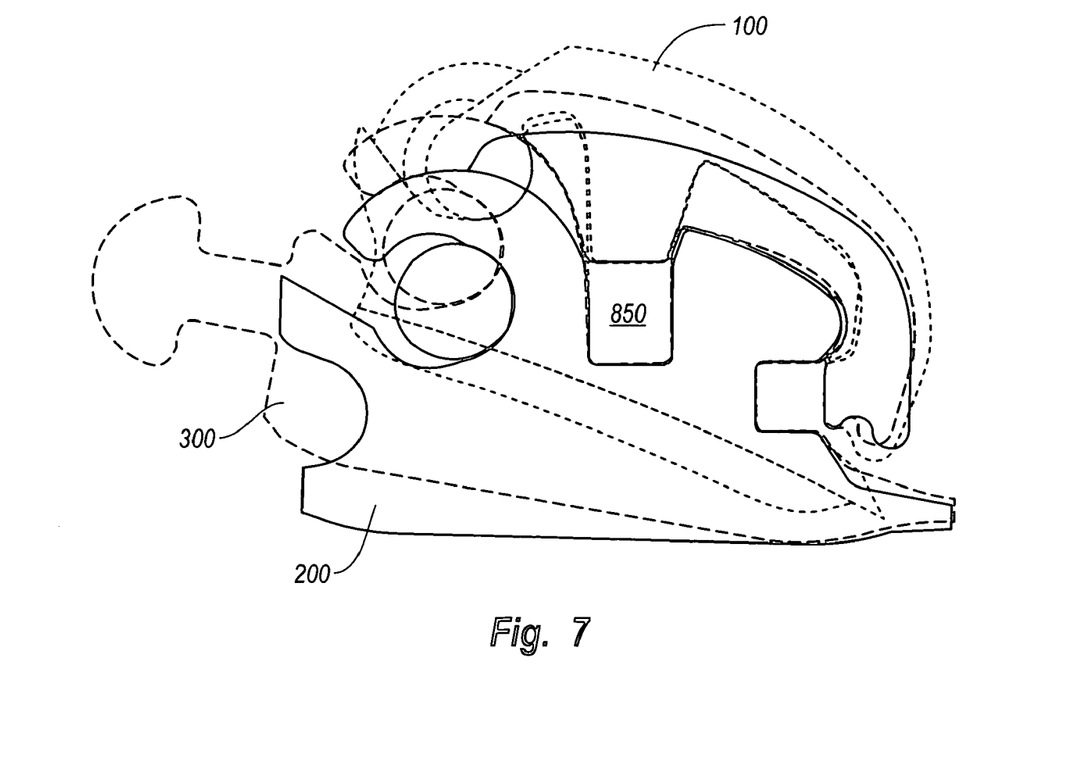
FIG. 7 is a view of the orthodontic brackets of FIGS. 1A-3B where the plurality of brackets having substantially aligned arch wire slots are viewed from the perspective of an evenly curved arch wire retained within the brackets.

FIG. 7 shows exemplary orthodontic brackets 100, 200, and 300. The plurality of brackets having substantially aligned arch wire slots are viewed from the perspective of evenly curved arch wire 850 retained within the brackets.

According to one embodiment, when in an aligned configuration, the arch wire slots of the brackets of the bracket system are aligned to within less than about 1 mm, more preferably within less than about 0.5 mm, and most preferably within less than about 0.2 mm.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An orthodontic bracket system comprising a plurality of orthodontic brackets, at least two of said brackets being sized and configured for use with differently sized and/or shaped teeth of a patient during an orthodontic treatment procedure, a first of said brackets being configured for attachment to a first tooth having a size and/or shape, the first bracket comprising:
   a bracket base having a bonding surface for attaching the bracket base of the first bracket to the first tooth;
   a primary arch wire slot;
   a secondary arch wire slot lying in a different plane than the primary arch wire slot; and
   a ligation cover movable between an open, non-ligating position, in which the primary and secondary arch wire slots are unoccluded by the ligation cover, and a closed, ligating position, in which the primary and secondary arch wire slots are occluded by the ligation cover, and an elongate film hinge attached at one end to the bracket base and at an opposite end to the ligation cover so as to hinged connect the ligation cover to the bracket base,
   the primary and secondary arch wire slots of the first bracket having a first special orientation relative to the bonding surface of the bracket base;
   a second of said brackets being configured for attachment to a second tooth having a size and/or shape different than the first tooth, the second bracket comprising:

a bracket base having a bonding surface for attaching the bracket base of the second bracket to the second tooth;
a primary arch wire slot; and
a secondary arch wire slot lying in a different plane than the primary arch wire slot,
the primary and secondary arch wire slots of the second bracket having a second special orientation relative to the bonding surface of the bracket base such that the orientation of the primary arch wire slot of the second bracket is different than the orientation of the primary arch wire slot of the first bracket and the orientation of the secondary arch wire slot of the second bracket is different than the orientation of the secondary arch wire slot of the first bracket so that, when the first and second teeth of different size and/or shape have become properly aligned as a result of the orthodontic treatment procedure, the primary arch wire slot of the first bracket will be substantially aligned with the primary arch wire slot of the second bracket in a first plane, and the secondary arch wire slot of the first bracket will be substantially aligned with the secondary arch wire slot of the second bracket in a second plane in order for the teeth to be moved in two different directions during treatment.

2. An orthodontic bracket system as recited in claim 1, wherein the plurality of orthodontic brackets are configured for placement on either the upper or lower dental arch.

3. An orthodontic bracket system as recited in claim 2, wherein the bracket system comprises from two to fourteen orthodontic brackets.

4. An orthodontic bracket system as recited in claim 1:
the primary arch wire slot of each bracket being positioned relative to the bracket base so that, when the patient's teeth have become properly aligned as a result of the orthodontic treatment procedure, the primary arch wire slots of all the brackets will be substantially aligned relative to a primary arch wire that lies substantially on a first plane and that is substantially devoid of bends that lie off the first plane; and
the secondary arch wire slot of each bracket being positioned relative to the bracket base so that, when the patient's teeth have become properly aligned as a result of the orthodontic treatment procedure, the secondary arch wire slots of all the brackets will be substantially aligned relative to a secondary arch wire that lies substantially on a second plane and that is substantially devoid of bends that lie off the second plane.

5. An orthodontic bracket system as recited in claim 1, wherein the primary and secondary arch wire slots in each bracket of the system are positioned relative to the bonding surface of that bracket such that, when the patient's teeth have become properly aligned as a result of the orthodontic treatment procedure, the primary arch wire slots of all the brackets are aligned to within less than about 1 mm in a first plane and the secondary arch wire slots of all the brackets are aligned to within less than about 1 mm in a second plane.

6. An orthodontic bracket system as recited in claim 1, wherein the primary and secondary arch wire slots in each bracket of the system are positioned relative to the bonding surface of that bracket such that, when the patient's teeth have become properly aligned as a result of the orthodontic treatment procedure, the primary arch wire slots of all the brackets are aligned to within less than about 0.5 mm in a first plane and the secondary arch wire slots of all the brackets are aligned to within less than about 0.5 mm in a second plane.

7. An orthodontic bracket system as recited in claim 1, wherein the primary and secondary arch wire slots in each bracket of the system are positioned relative to the bonding surface of that bracket such that, when the patient's teeth have become properly aligned as a result of the orthodontic treatment procedure, the primary arch wire slots of all the brackets are aligned to within less than about 0.2 mm in a first plane and the secondary arch wire slots of all the brackets are aligned to within less than about 0.2 mm in a second plane.

8. An orthodontic bracket system as recited in claim 1, each orthodontic bracket further comprising a ligation cover movable between an open, non-ligating position and a closed, ligating position and a latch mechanism that selectively locks and unlocks the ligation cover in the closed, ligating position.

9. An orthodontic bracket system as recited in claim 8, wherein the latch mechanism comprises a latch bump within a side of the bracket base and a latch projection extending from an end of the ligation cover, the latch projection being configured so as to snap over the latch bump and lock the ligation cover to the bracket base in the closed, ligating position.

10. An orthodontic bracket system as recited in claim 8, wherein the latch mechanism comprises an angled keyway within a side of the bracket base and a locking tongue extending from an end of the ligation cover, the locking tongue being configured so as to selectively fit within the angled keyway and lock the ligation cover to the bracket base in the closed, ligating position.

11. An orthodontic bracket system as recited in claim 1, further comprising a hinge guide structure, disposed on the ligation cover, which provides a curved surface around which the elongate film hinge bends when the ligation cover is selectively moved relative to the bracket base so that the film hinge bends over substantially its entire length.

12. An orthodontic bracket system as recited in claim 11, wherein the hinge guide structure comprises a curved surface of the bracket base adjacent to the elongate film hinge.

13. An orthodontic bracket system as recited in claim 11, wherein the hinge guide structure comprises a curved surface, proximal to the film hinge, of a cam structure that is attached to an inner surface of the ligation cover and that extends toward the bracket base.

14. An orthodontic bracket system as recited in claim 13, wherein the curved surface interacts with the elongate film hinge so as to distribute bending forces along substantially the entire length of the elongate film hinge when the ligation cover is selectively moved relative to the bracket base.

15. An orthodontic bracket system as recited in claim 13, wherein the cam structure comprises a camming surface, distal to the film hinge, that interacts with the bracket base so as to bias the ligation cover toward the open, non-ligating position.

16. An orthodontic bracket system as recited in claim 1, wherein the primary and secondary arch wire slots of the first bracket lie in planes that are substantially perpendicular to each other and wherein the primary and secondary arch wire slots of the second bracket lie in planes that are substantially perpendicular to each other.

17. An orthodontic bracket system comprising a plurality of differently sized and shaped orthodontic brackets configured for use with differently sized and shaped teeth of a patient in order to provide concurrently movement of the patient's teeth in multiple directions during treatment, each bracket sized and configured to be placed on a particular tooth of a patient during an orthodontic treatment procedure, each bracket comprising:
a bracket base having a bonding surface for attaching the bracket base of the first bracket to the first tooth;

primary and secondary arch wire slots that lie in different planes, the primary and secondary arch wire slots of each bracket being positioned relative to the bracket base so that, when the patient's teeth have become properly aligned as a result of the orthodontic treatment procedure, the primary arch wire slots of all the brackets will be substantially aligned with each other relative to a primary arch wire that lies substantially on a first plane and that is substantially devoid of bends that lie off the first plane, and the secondary arch wire slots of all the brackets will be substantially aligned with each other relative to a secondary arch wire that lies substantially on a second plane and that is substantially devoid of bends that lie off the second plane, wherein the primary arch wire slots of at least some of the brackets differ as to their orientation relative to the bonding surface as among other of the brackets and wherein the secondary arch wire slots of at least some of the brackets differ as to their orientation relative to the bonding surface as among other of the brackets;

a ligation cover connected to the bracket base and selectively movable relative to the bracket base between an open, non-ligating position, in which the primary and secondary arch wire slots are unclouded by the ligation cover, and a closed, ligating position, in which the primary and secondary arch wire slots are occluded by the ligation cover;

an elongate film hinge attached at one end to the bracket base and at an opposite end to the ligation cover so as to hinged connect the ligation cover to the bracket base; and a hinge guide structure, disposed on the ligation cover or bracket base, which provides a curved surface around which the elongate film hinge bends when the ligation cover is selectively moved relative to the bracket base so that the film hinge bends over substantially its entire length.

18. An orthodontic bracket system as recited in claim 17, wherein the curved surface interacts with the elongate film hinge so as to distribute bending forces along substantially the entire length of the elongate film hinge when the ligation cover is selectively moved relative to the bracket base.

19. An orthodontic bracket system as recited in claim 17, wherein the hinge guide structure comprises a curved surface, proximal to the film hinge, of a cam structure that is attached to an inner surface of the ligation cover and that extends toward the bracket base.

20. An orthodontic bracket system as recited in claim 17, wherein the cam structure comprises a camming surface, distal to the film hinge, that interacts with the bracket base so as to bias the ligation cover toward the open, non-ligating position.

21. A method of concurrently moving a patient's teeth in multiple directions without substantial bending of arch wires during the course of treatment, the method comprising:

providing an orthodontic bracket system as recited in claim 17;

bonding each orthodontic bracket to one of a person's teeth; and inserting a primary arch wire into the primary arch wire slots of said orthodontic brackets and a secondary arch wire into the secondary arch wire slots of said orthodontic brackets in order to concurrently move the person's teeth in multiple directions without substantial bending of the primary and secondary arch wires, the primary arch wire slots of all the brackets becoming substantially aligned with each other without substantial bending of the primary arch wire and the secondary arch wire slots of all the brackets becoming substantially aligned with each other without substantial bending of the secondary arch wire when the person's teeth have become properly aligned.

22. An orthodontic bracket system as recited in claim 17, wherein the primary and secondary arch wire slots of at least some of the brackets lie in planes that are substantially perpendicular to each other.

23. An orthodontic bracket system comprising a plurality of differently sized and shaped orthodontic brackets configured for use with differently sized and shaped teeth of a patient in order to provide concurrently movement of the patient's teeth in multiple directions during treatment, each bracket sized and configured to be placed on a particular tooth of a patient during an orthodontic treatment procedure, each bracket comprising:

a bracket base having a bonding surface for attaching the bracket base of the first bracket to the first tooth;

primary and secondary arch wire slots that lie in different planes, the primary and secondary arch wire slots of each bracket being positioned relative to the bracket base so that, when the patient's teeth have become properly aligned as a result of the orthodontic treatment procedure, the primary arch wire slots of all the brackets will be substantially aligned with each other relative to a primary arch wire that lies substantially on a first plane and that is substantially devoid of bends that lie off the first plane, and the secondary arch wire slots of all the brackets will be substantially aligned with each other relative to a secondary arch wire that lies substantially on a second plane and that is substantially devoid of bends that lie off the second plane, wherein the primary arch wire slots of at least some of the brackets differ as to their orientation relative to the bonding surface as among other of the brackets and wherein the secondary arch wire slots of at least some of the brackets differ as to their orientation relative to the bonding surface as among other of the brackets;

a ligation cover connected to the bracket base and selectively movable relative to the base between an open, non-ligating position and a closed, ligating position; and a joint pivotally connecting the ligation cover to the bracket base and configured so as to permit the ligation cover to have multiple degrees of freedom of movement relative to the base while in the open, non-ligating position.

24. A method of concurrently moving a patient's teeth in multiple directions without substantial bending of arch wires during the course of treatment, the method comprising:

providing an orthodontic bracket system as recited in claim 23;

bonding each orthodontic bracket to one of a person's teeth; and inserting a primary arch wire into the primary arch wire slots of said orthodontic brackets and a secondary arch wire into the secondary arch wire slots of said orthodontic brackets in order to concurrently move the person's teeth in multiple directions without substantial bending of the primary and secondary arch wires, the primary arch wire slots of all the brackets becoming substantially aligned with each other without substantial bending of the primary arch wire and the secondary arch wire slots of all the brackets becoming substantially aligned with each other without substantial bending of the secondary arch wire when the person's teeth have become properly aligned.

* * * * *

UNITED STATES PATENT AND TRADEMARK OFFICE
CERTIFICATE OF CORRECTION

PATENT NO. : 7,234,935 B2
APPLICATION NO. : 10/836014
DATED : June 26, 2007
INVENTOR(S) : Abels et al.

Page 1 of 1

It is certified that error appears in the above-identified patent and that said Letters Patent is hereby corrected as shown below:

<u>Column 1</u>
Line 60, after "arch" insert --wires.--

<u>Column 5</u>
Line 4, before "will" remove [are]
Line 20, before "secondary" change "an" to --a--

<u>Column 6</u>
Line 12, change "hinged" to --hingedly--
Line 26, change "hinged" to --hingedly--

<u>Column 8</u>
Line 60, change "hinged" to --hingedly--

<u>Column 11</u>
Line 30, change "hinged" to --hingedly--
Line 47, change "17" to --19--

Signed and Sealed this

Twenty-fifth Day of December, 2007

JON W. DUDAS
*Director of the United States Patent and Trademark Office*